United States Patent
Chen et al.

(10) Patent No.: US 9,851,397 B2
(45) Date of Patent: Dec. 26, 2017

(54) ELECTROMIGRATION TESTING OF INTERCONNECT ANALOGUES HAVING BOTTOM-CONNECTED SENSORY PINS

(71) Applicant: GLOBALFOUNDRIES INC., Grand Cayman (KY)

(72) Inventors: Fen Chen, Williston, VT (US); Cathryn J. Christiansen, Huntington, VT (US); Deborah M. Massey, Jericho, VT (US); Prakash Periasamy, Essex Junction, VT (US); Michael A. Shinosky, Jericho, VT (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 320 days.

(21) Appl. No.: 14/635,125

(22) Filed: Mar. 2, 2015

(65) Prior Publication Data
US 2016/0258998 A1    Sep. 8, 2016

(51) Int. Cl.
*G01R 31/00* (2006.01)
*G01R 31/28* (2006.01)
(Continued)

(52) U.S. Cl.
CPC ........... *G01R 31/2858* (2013.01); *G01N 1/00* (2013.01); *H01L 21/00* (2013.01); *H01L 2221/00* (2013.01)

(58) Field of Classification Search
CPC ....... H01L 21/00; H01L 2221/00; G01N 1/00; G01N 2201/00
See application file for complete search history.

(56) References Cited

U.S. PATENT DOCUMENTS 5,291,142 A    3/1994 Ohmi
5,532,600 A    7/1996 Hoshino
(Continued)

FOREIGN PATENT DOCUMENTS

CN    103811467 A    5/2014
JP    11214628 A    8/1999
(Continued)

OTHER PUBLICATIONS

Sukharev et al., "Microstructure Effect on EM-Induced Degradations in Dual Inlaid Copper Interconnects", IEEE Transactions on Device and Materials Reliability, vol. 9, No. 1, Mar. 2009, © 2009 IEEE, Digital Object Identifier 10.1109/TDMR.2008.2011642.
(Continued)

*Primary Examiner* — Huy Q Phan
*Assistant Examiner* — Temilade Rhodes-Vivour
(74) *Attorney, Agent, or Firm* — David Cain; Hoffman Warnick LLC

(57) ABSTRACT

A system for electromigration testing is disclosed. The system includes a conductive member, a cap layer of insulative material over at least a portion of a top surface of the conductive member, a cathode conductively connected to a first end of the conductive member; an anode conductively connected to a second end of the conductive member, and a current source conductively connected to the cathode and the anode. A plurality of sensory pins are disposed along a length of the conductive member between the first end and the second end of the conductive member. The sensory pins are conductively connected to a bottom surface of the conductive member. At least one measurement device is conductively connected to at least one sensory pin of the plurality of sensory pins. The at least one measurement device determines a resistance of at least one portion of the conductive member.

18 Claims, 8 Drawing Sheets

(51) Int. Cl.
 *H01L 21/00* (2006.01)
 *G01N 1/00* (2006.01)

(56) References Cited

U.S. PATENT DOCUMENTS

| | | | |
|---|---|---|---|
| 6,306,732 B1 * | 10/2001 | Brown | H01L 21/7681 257/E21.579 |
| 6,724,214 B2 | 4/2004 | Manna et al. | |
| 6,819,124 B1 * | 11/2004 | Allee | G01R 31/2858 324/525 |
| 7,304,485 B2 | 12/2007 | Cappelletti et al. | |
| 7,394,273 B2 | 7/2008 | Hsu et al. | |
| 7,719,302 B2 | 5/2010 | Hsu et al. | |
| 7,764,078 B2 | 7/2010 | Feustel et al. | |
| 7,840,916 B2 | 11/2010 | Hsu et al. | |
| 8,237,458 B2 | 8/2012 | Federspiel | |
| 8,253,423 B2 | 8/2012 | Lee et al. | |
| 8,323,990 B2 | 12/2012 | Shi et al. | |
| 2003/0080085 A1 * | 5/2003 | Greenberg | A61K 9/0009 216/20 |
| 2005/0072919 A1 * | 4/2005 | Meyer | G01N 23/04 250/307 |
| 2009/0294973 A1 * | 12/2009 | Chanda | H01L 23/528 257/767 |
| 2011/0074459 A1 | 3/2011 | Ruan et al. | |
| 2011/0241124 A1 * | 10/2011 | Kurz | H01L 21/28518 257/379 |
| 2013/0106452 A1 | 5/2013 | Chen et al. | |
| 2015/0177319 A1 * | 6/2015 | Yi | H01L 22/34 324/762.01 |

FOREIGN PATENT DOCUMENTS

| | | |
|---|---|---|
| TW | 200506393 A | 2/2005 |
| TW | I257002 B | 6/2006 |
| TW | 200907367 A | 2/2009 |

OTHER PUBLICATIONS

Li et al., "Copper Electromigration Failure Times Evaluated Over a Wide Range of Voiding Phases", pp. EM.1.1-EM.1.4, © 2012 IEEE.
Wang et al., "Multi-site On-chip Current Sensor for Electromigration Monitoring", 2011 IEEE 54th International Midwest Symposium on Circuits and Systems, pp. 1-4, DOI: 10.1109/MWSCAS.2011.6026283.
Examination Report and English translation thereof for Taiwan Patent Application No. 105101678, dated Apr. 5, 2017, (GFBT-0470-TW) 7 pages.

* cited by examiner

ELECTROMIGRATION TESTING OF INTERCONNECT ANALOGUES HAVING BOTTOM-CONNECTED SENSORY PINS

BACKGROUND OF THE INVENTION

The present invention relates generally to the field of integrated circuit test systems and, more particularly, to electromigration test systems and methods for using electromigration test systems.

Electromigration (EM) is the transport of material caused by the gradual movement of metal atoms in a conductor due to the transfer of momentum between conducting electrons and the metal atoms. Electromigration-induced voids nucleate when metallic ions are dislodged from the crystal lattice of the conductor. Voids can grow, migrate, and agglomerate. Electromigration can also induce extrusion in regions where metal atoms agglomerate. Void agglomeration and extrusion generally occur at opposite ends of a conductive member. Voids generally agglomerate near an electron source, and extrusion generally occurs near an electron drain. Electromigration can have negative effects, such as decreasing the reliability of integrated circuits. Integrated circuits can fail due to electromigration when voids grow or agglomerate and break interconnects and/or when electromigration-induced extrusion causes a short circuit.

A typical electromigration test system passes a current through an interconnect and measures resistance as a function of time in order to detect electromigration. Voids generally nucleate at defective sites in the interconnect crystal lattice. Void growth and agglomeration reduces the local cross-sectional area of the interconnect over time, and the resistance of the interconnect increases as a result.

SUMMARY

According to one embodiment of the present disclosure, a system for electromigration testing is provided. The system includes: a conductive member; a cap layer of insulative material over at least a portion of a top surface of the conductive member; a cathode conductively connected to a first end of the conductive member; an anode conductively connected to a second end of the conductive member, wherein the conductive member conductively connects the anode and the cathode; a current source conductively connected to the cathode and anode; wherein the current source provides a current that flows through the conductive member; a plurality of sensory pins disposed along a length of the conductive member between the first end and the second end of the conductive member, the sensory pins conductively connected to a bottom surface of the conductive member; and at least one measurement device conductively connected to at least one sensory pin of the plurality of sensory pins, wherein the at least one measurement device determines a resistance of at least one portion of the conductive member.

According to another embodiment of the present disclosure, a method for electromigration testing is provided. The method includes causing a current to flow through a conductive member; and determining a resistance of at least one portion of the conductive member using at least one measurement device, and wherein: a cap layer of insulative material is disposed over at least a portion of a top surface of the conductive member, a plurality of sensory pins is disposed along a length of the conductive member between a first end of the conductive member and a second end of the conductive member, each sensory pin of the plurality of sensory pins is conductively connected to a bottom surface of the conductive member, each at least one portion of the conductive member includes at least one sensory pin of the plurality of the sensory pins, and the at least one measurement device is conductively connected to at least one sensory pin of the plurality of sensory pins According to another embodiment of the present disclosure, an apparatus for electromigration testing is provided. The apparatus includes a plurality of conductive members embedded in a substrate, wherein each conductive member of the plurality of conductive member comprises: a first end conductively connected to a first active via; a second end conductively connected to a second active via; and a plurality of sensory pins disposed along a length of the conductive member between the first end and the second end of the conductive member, wherein each sensory pin has a first end that is conductively connected to a bottom surface of the conductive member, and wherein each sensory pin has a second end that is at least partially exposed.

DETAILED DESCRIPTION

Figure 1A:
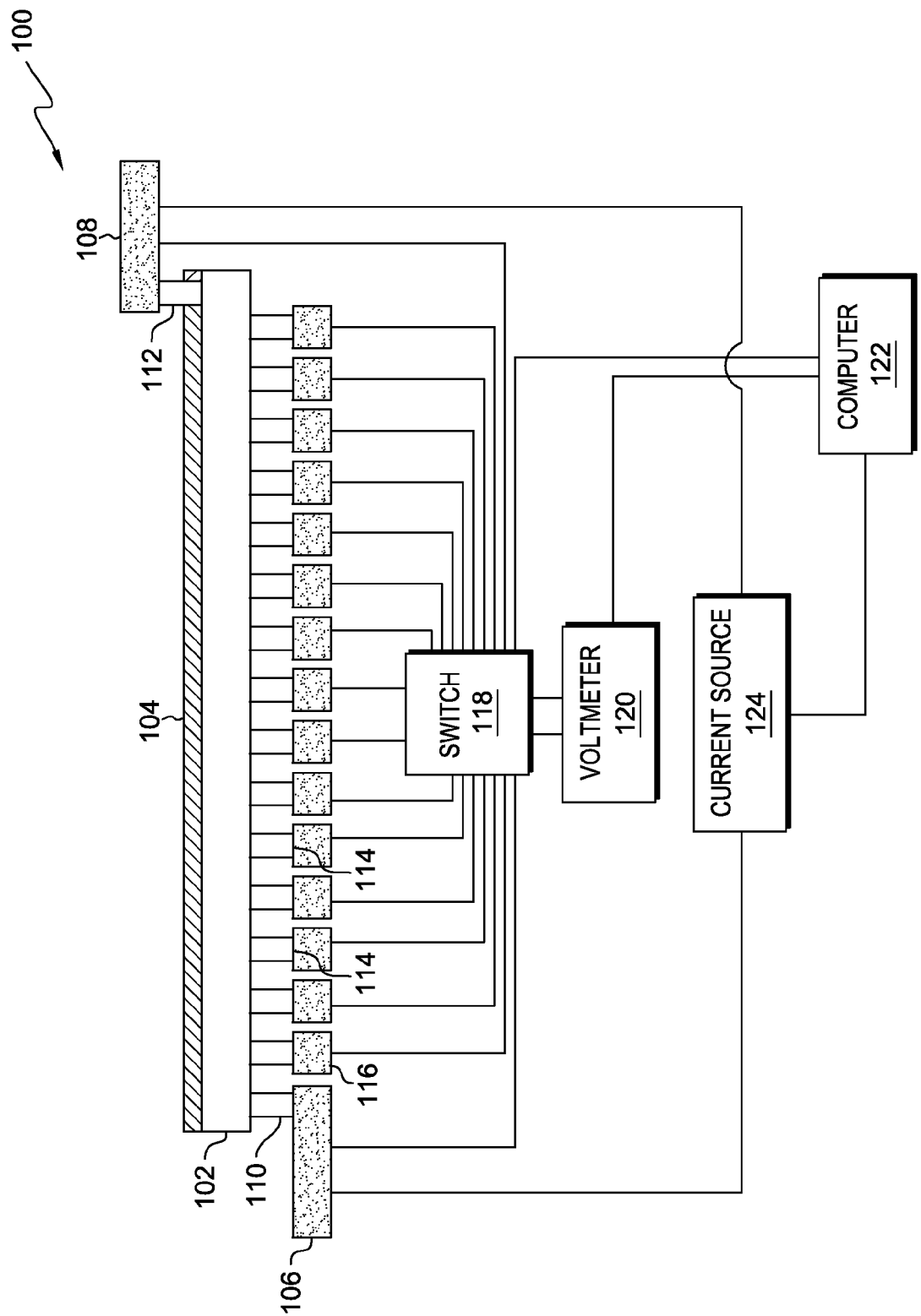
FIG. 1A is a functional block diagram of an electromigration test system, in accordance with an embodiment of the present disclosure.

Embodiments of the present invention recognize a need to study void evolution in the nucleation and growth phases. Electromigration is of increasing concern as integrated circuit technology advances to smaller and smaller nodes. Smaller nodes have required a transition from aluminum interconnects to copper interconnects. While copper has a lower bulk resistance and a higher EM resistance than aluminum, copper interconnects require liner materials to prevent diffusion of copper into surrounding materials. Liner thickness and circuit voltage, however, generally do not scale at the same rate as the transverse cross-sectional area of interconnects at each node. Consequently, current density and electromigration concerns generally increase as node size decreases. Moreover, copper interconnects generally require post-deposition processing that can induce defects in copper interconnect crystal lattices. For example, back end of line (BEOL) processing can include deposition and chemical-mechanical planarization steps, wherein copper is deposited on an insulator in a thick layer that overfills interconnect trenches, and a polishing pad removes the copper overburden before a capping layer of insulator is applied. The polishing step, however, can induce defects in the copper interconnect lattices. Understanding when and where voids nucleate is of increasing concern in order to improve BEOL processes and EM reliability kinetic modeling (e.g., modelling electromigration and extrusion).

Traditional EM test systems are of limited value to efforts to improve BEOL processes and EM reliability kinetic modeling. Traditional EM test systems measure the average relative resistance change over time of an interconnect as a whole, but the absolute resistance increase induced by void nucleation and early-stage void growth is generally small compared to the base, time-zero (T(0)) resistance of the interconnect as a whole. Moreover, present node sizes (e.g., 22 nm and 14 nm nodes) have significantly higher T(0) resistance than legacy node sizes. In general, traditional EM test systems lack sufficient sensitivity at present node sizes to reliably detect void nucleation and void growth. Moreover, traditional EM test systems cannot determine the locations of void nucleation sites and growing voids. While void nucleation and growth can be observed via scanning electron microscopy (SEM) or transmission electron microscopy (TEM) during in situ electromigration testing, SEM and TEM sample preparation is time consuming, which renders large sample sizes impractical.

Embodiments of the present invention provide an EM test system with improved void detection sensitivity. Embodiments of the EM test system electrically detect and characterize pre-existing voids and void evolution. Void evolution includes void nucleation, void growth, void migration, and void agglomeration. Embodiments of the EM test system also determine approximate locations of voids. Embodiments of the EM test system may help improve BEOL processes, for example, by identifying defect-inducing processes. Embodiments of the EM test system may also help improve EM reliability kinetic models, for example, by identifying likely void nucleation sites.

The present disclosure will now be described in detail with reference to the Figures. FIG. 1A is a functional block diagram depicting EM test system 100, in accordance with an embodiment of the present disclosure. EM test system 100 includes conductive member 102. Conductive member 102 is an analogue of an interconnect. EM test system 100 determines the EM characteristics of conductive member 102 in order to, at least in part, generate data for use in modelling electromigration in interconnects. Conductive member 102 can be made of any conductive material that is suitable for use as an interconnect. Conductive member 102 is also shaped and sized to approximate an interconnect.

Figure 1B:
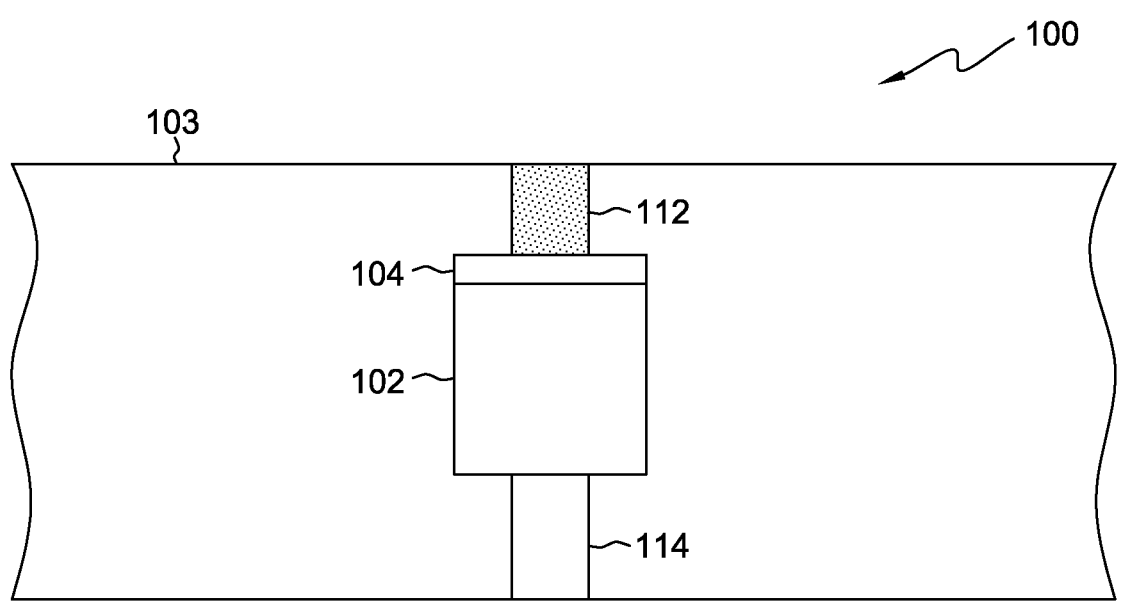
FIG. 1B is a functional block diagram that depicts an edge-on view of wafer that includes a substrate and embedded elements of the electromigration test system depicted in FIG. 1A.

FIG. 1B is a functional block diagram that depicts, from one end of conductive member 102, a cross-section of a wafer that includes substrate 103 and elements of EM test system 100. In some embodiments, substrate 103 is one or more layers of insulative or dielectric material (e.g., monocrystalline silicon) that form a wafer that includes one or more conductive members. In some embodiments, a liner material (not shown for clarity; e.g., a material that is different from substrate 103) is interposed between one or more surfaces of conductive member 102 and substrate 103. A portion of substrate 103 (or, in some embodiments, a portion of the liner) forms cap layer 104. Cap layer 104 is in physical contact with at least a portion of a top surface of conductive member 102. Portions of the top surface of conductive member 102 that are connected to cap layer 104 create a top surface/cap layer interface. FIG. 1B also depicts active via 112 and one sensory pin of sensory pins 114 embedded in substrate 103. Active via 110, active via 112, and sensory pins 114 are at least partially exposed to respective surfaces of substrate 103 and can conductively connect to external devices as described hereafter with reference to FIG. 1A.

In the embodiment depicted in FIG. 1A, EM test system 100 includes cathode 106 and anode 108. Cathode 106 is electrically connected to a first end of conductive member 102, referred to as the "V1" end, through active via 110 (i.e., "via V1"). Anode 108 is electrically connected to a second end of conductive member 102, referred to as the "V2" end, through active via 112 (i.e., "via V2"). Cathode 106 and anode 108 are also electrically connected to current source 124. Current source 124 provides a current that flows through conductive member 102. Cathode 106 and anode 108 can be made of aluminum, copper, tungsten, or any other suitable material.

EM test system 100 includes sensory pins 114. Sensory pins 114 are distributed longitudinally, in a row, between the V1 end of conductive member 102 and the V2 end of conductive member 102 (e.g., between the cathode 106 and the anode 108). Sensory pins 114 are connected to a bottom surface of conductive member 102. The bottom surface of conductive member 102 is opposite to the top surface of conductive member 102. In some embodiments, sensory pins 114 are, in effect, vias that are integrated with, and extend from, the bottom surface of conductive member 102. For example, forming a trench and an appropriate number of vias in a silicon wafer and filling the trench and vias with copper can produce conductive member 102 and sensory pins 114 as part of a dual-Damascene process. In other embodiments, conductive member 102 and sensory pins 114 are separate features that are in physical contact. For example, the trench and vias can be filled in separate Damascene processes, wherein the vias are filled first, and the trench is filled afterwards. Separate Damascene processes can allow for conductive member 102 and sensory pins 114 to be made from different materials or allow for the inclusion of material between conductive member 102 and sensory pins 114.

Sensory pins 114 are operatively connected to the bottom surface of conductive member 102 to, at least in part, provide a test system that approximates the electromigration characteristics of a typical interconnect. As described herein, BEOL processes can create defects in the crystal lattices of interconnects. Chemical-mechanical planarization processes are particularly likely to create defects on the top surfaces of interconnects. Experimental results indicate that void evolution at the top-surface/cap-layer interface generally determines the EM degradation characteristics of typical copper interconnects. Sensory pins, however, can alter void evolution characteristics. For example, sensory pins provide a source of additional copper atoms that can increase the EM time-to-failure. In addition, sensory pins can introduce large blocking grains into an otherwise polycrystalline system that slow down copper atom diffusion and increase the EM time-to-failure. Sensory pins 114 are operatively connected to the bottom surface of conductive member 102 to, at least in part, minimize the effects of these mechanisms on the void evolution characteristics of the top-surface/cap-layer interface. Other configurations, however, can significantly alter EM degradation characteristics. For example, longitudinally distributed sensory pins that extend out from the sides of a test interconnect in the plane of the wafer (i.e., "in-plane" sensory pins) can alter void evolution characteristics as described herein. Experiments show that the EM time-to-failure of configurations that include in-plane sensory pins can be approximately twice as long as the EM time-to-failure for an interconnect that is not connected to sensory pins. In contrast, interconnects tested using EM test system 100 have similar EM time-to-failure values as interconnects that are not connected to sensory pins.

In various embodiments, sensory pins 114 include any number of individual sensory pins. In practice, however, approximately 20 to 45 sensory pins provide acceptable void detection sensitivity and void location-finding resolution. The spacing between sensory pins 114 is approximately 20 times to approximately 45 times smaller than the total length of conductive member 102. The spacing between sensory pins 114 depends on the number of sensory pins used and the length of conductive member 102. Sensory pins 114, cathode 106, and anode 108 divide conductive member 102 into a plurality of test sections. A test section is defined by the space between adjacent sensor pins or the space between a sense lead (e.g., via 110, via 112) connected to cathode 106 or anode 108 and a respective, adjacent sensory pin. In some embodiments, the spacing between sensory pins 114, cathode 106, and anode 108 varies. In the other embodiments, the spacing is uniform.

Sensory taps 116 operatively connect sensory pins 114 to switch 118. The number of sensory taps 116 is equal to or greater than the number of sensory pins (sensory taps 116 can also connect switch 118 to leads that are connected to anode 106 or anode 108). In some embodiments, EM test system 100 includes multiple conductive members that are embedded in substrate 103 (of which conductive member 102 is an example) to form, at least in part, a wafer, wherein each conductive member is connected to a number of sensory pins. In such embodiments, sensory taps 116 are removably connected to sensory pins 114 and can removably connect to a different set of sensory pins. After conductive member 102 is stressed to failure, for example, cathode 106, anode 108, and sensory taps 116 can be moved and connected to another conductive member via a different set of sensory pins and active vias.

In the embodiment depicted in FIG. 1A, switch 118 is operatively connected to voltmeter 120. Switch 118 includes a plurality of relays and is configured to allow voltmeter 120 to measure voltages between two sensory pins of sensory pins 114, between cathode 106 and a sensory pin, and between anode 108 and a sensory pin. In some embodiments, switch 118 is configured to allow voltmeter 120 to measure the voltage between any two sensory pins. In other embodiments, switch 118 is configured to allow voltmeter 120 to measure the voltage between any two adjacent sensory pins (and between cathode 106 or anode 108 and their respective, adjacent sensory pins). In other words, switch 118 is configured to allow voltmeter 120 to measure voltages over a number of successive test sections. In some embodiments, voltmeter 120 can measure a voltage over a section of conductive member 102 that includes multiple test sections. Yet other embodiments omit switch 118 to provide each test section with a separate voltmeter. A person of ordinary skill in the art will understand that the resistance of each test section can be determined from measuring the voltage across a respective test section. EM test system 100 can be configured to measure any quantity that allows for a determination of the resistance or impedance of each test section. In general, EM test system 100 is configured to determine the resistance or impedance of each of a plurality of test sections using four-terminal sensing techniques.

In the embodiment depicted in FIG. 1A, computer 122 is operatively connected to switch 118, voltmeter 120, and current source 124. Computer 122 can be used to control the amount of current that current source 124 applies to conductive member 102. Computer 122 can also record, analyze, and display data obtained from voltmeter 120. Computer 122 also provides a user interface that allows a user to, among other things, choose a sampling interval and/or choose the amount of current that current source 124 provides to conductive member 102. In accordance with the sampling interval, computer 122 can direct switch 118 to connect voltmeter 120 to successive test sections (e.g., pairs of sensory pins or cathode 106 or anode 108 and their respective, adjacent sensory pins). Computer 122 can analyze the measurements for each test section and display a resistance spectrum that shows the resistance of each test section at a point in time. For example, FIGS. 2 to 7 depict examples of resistance spectra at "T(0)" and "T(n+x)."

Figure 2:
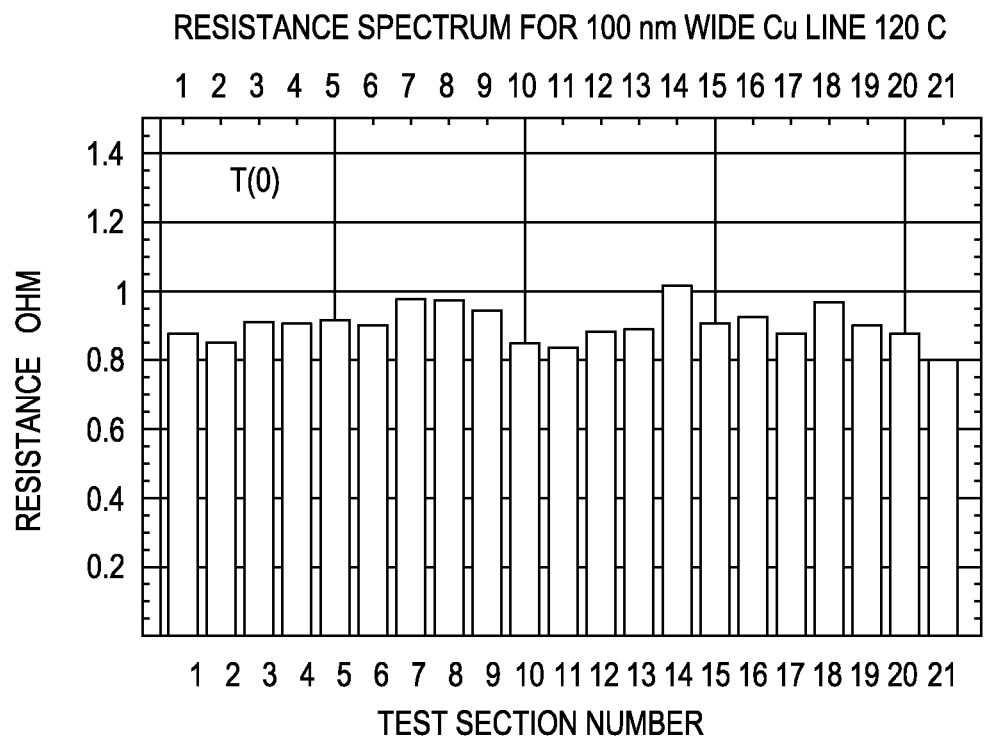
FIG. 2 is an example resistance spectrum of the electromigration test system depicted in FIG. 1A, in accordance with an embodiment of the present disclosure.

FIG. 2 depicts an example of a T(0) resistance spectrum. The T(0) resistance spectrum is obtained by applying an initial low current to conductive member 102 and determining the resistance of each test section. The T(0) resistance spectrum does not show obvious signs of the presence of a pre-existing void (e.g., a resistance that is significantly higher than that of other test sections), although test section 14 has the highest resistance at just over 1 ohm.

Figure 3:
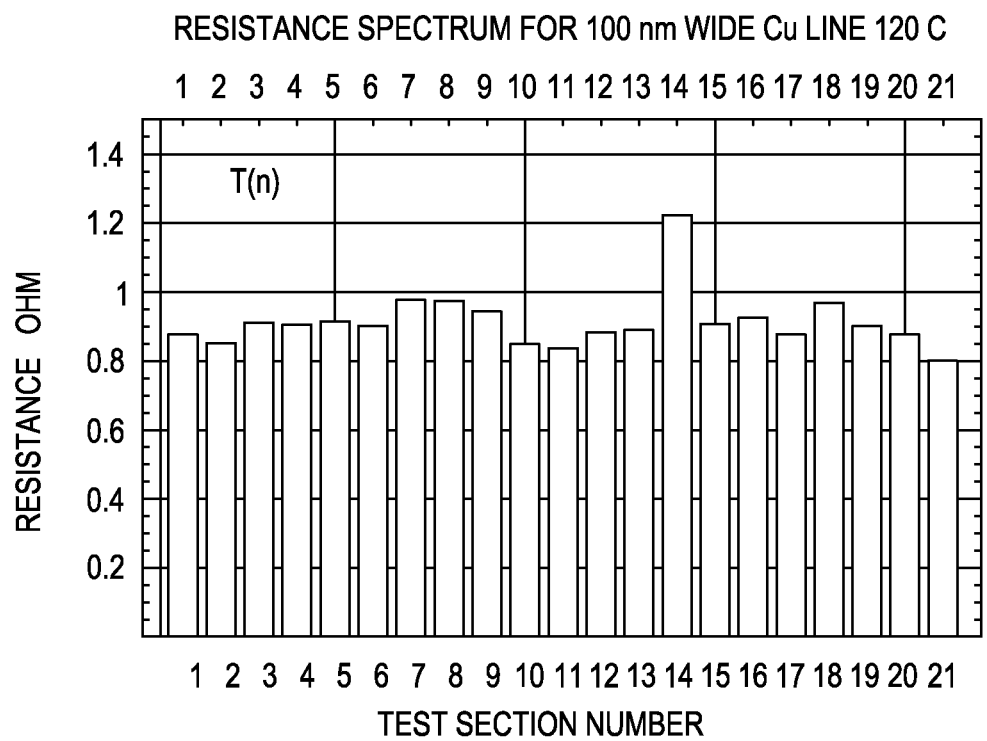
FIG. 3 is an example resistance spectrum of the electromigration test system depicted in FIG. 1A, in accordance with an embodiment of the present disclosure.

FIG. 3 depicts an example of a resistance spectrum at T(n). At T(n), voltmeter 120 has provided a stress current to conductive member 102 for n units of time (e.g., a count of minutes, hours, or days). In general, the stress current through conductive member 102 is higher than the current through a substantially similar interconnect under normal operating conditions in order to accelerate electromigration. In FIG. 3, the resistance of test section 14 has significantly increased compared to the resistance of section 14 at T(0). The increase in resistance of test section 14 between T(0) and T(n) indicates that, in this example, a void is growing within test section 14. As the void grows, the local cross-sectional area of test section 14 decreases and the current density increases. Consequently, the resistance of test section 14 increases.

Figure 4:
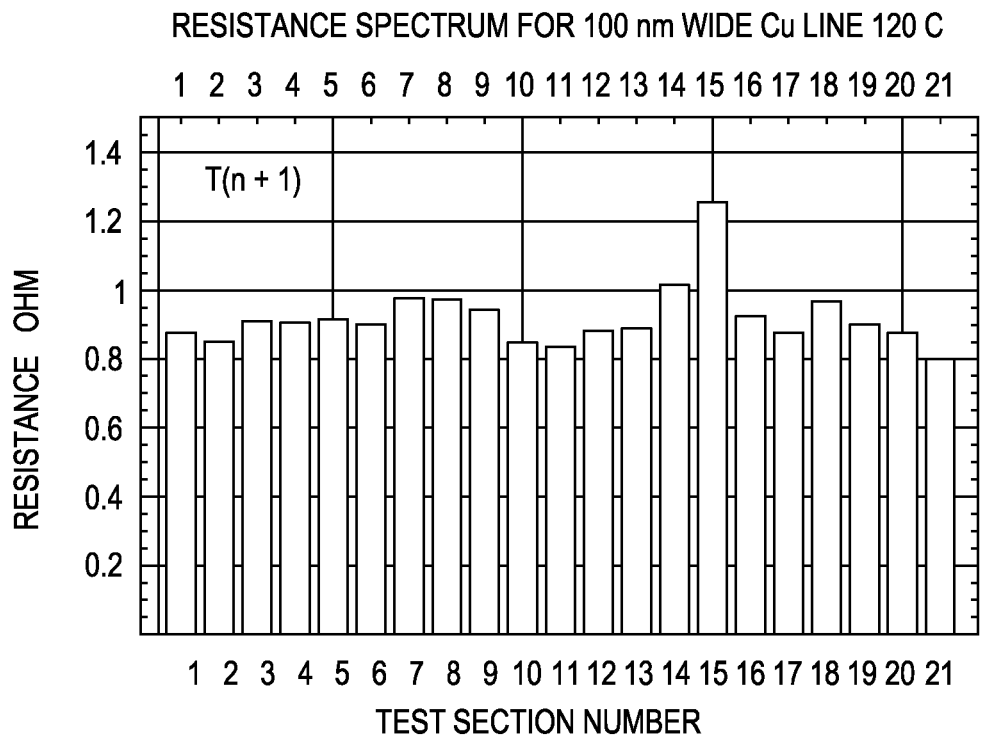
FIG. 4 is an example resistance spectrum of the electromigration test system depicted in FIG. 1A, in accordance with an embodiment of the present disclosure.

FIG. 4 depicts an example of a resistance spectrum at T(n+1). In FIG. 4, the resistance of test section 14 has decreased, but the resistance of test section 15 has increased significantly. The resistance of test section 15 at T(n+1) is comparable to the resistance of test section 14 at T(n). FIG. 4 indicates that the void that nucleated and grew in test section 14 from T(0) to T(n) and migrated to test section 15 between T(n) and T(n+1).

Figure 5:
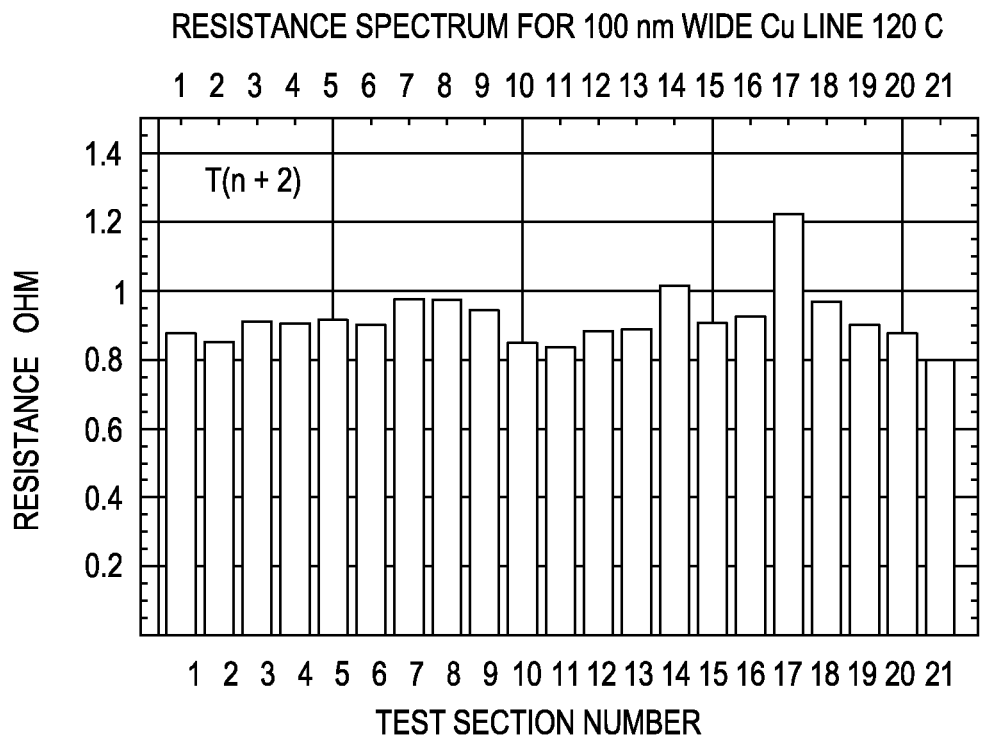
FIG. 5 is an example resistance spectrum of the electromigration test system depicted in FIG. 1A, in accordance with an embodiment of the present disclosure.

FIG. 5 depicts an example of a resistance spectrum at T(n+2). In FIG. 5, the resistance of test section 15 has decreased, but the resistance of test section 17 has increased significantly. FIG. 5 indicates that the void migrated from test section 15 to test section 17 between T(n+1) and T(n+2).

Figure 6:
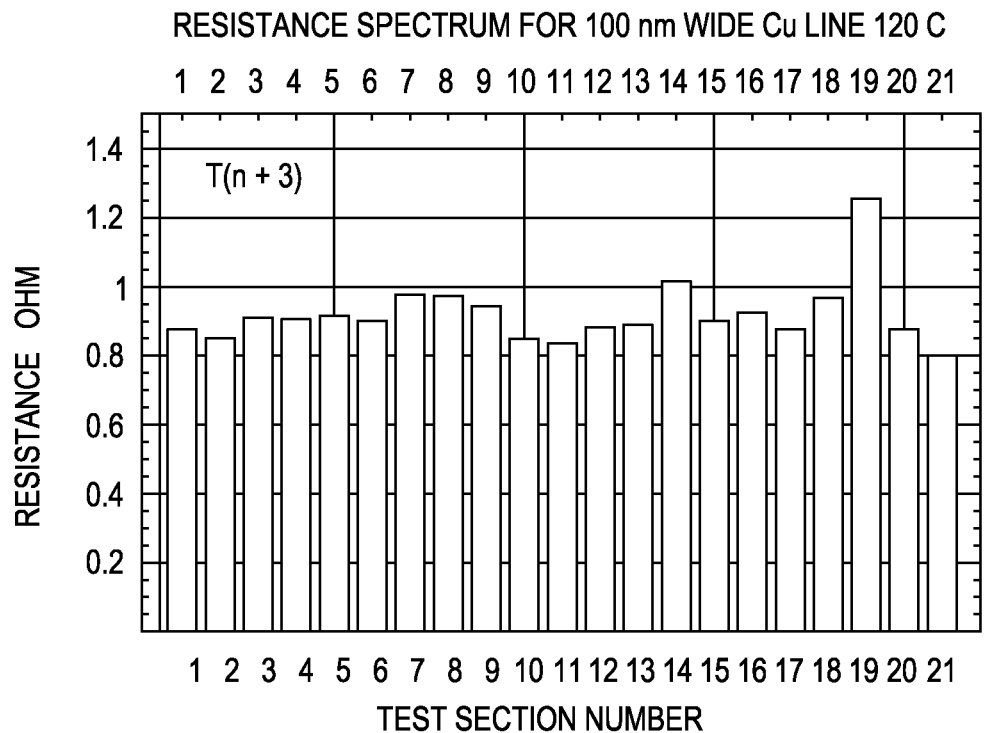
FIG. 6 is an example resistance spectrum of the electromigration test system depicted in FIG. 1A, in accordance with an embodiment of the present disclosure.

FIG. 6 depicts an example of a resistance spectrum at T(n+3). In FIG. 5, the resistance of test section 17 has decreased, but the resistance of test section 19 has increased significantly. FIG. 6 indicates that the void migrated from test section 17 to test section 19 between T(n+2) and T(n+3).

Figure 7:
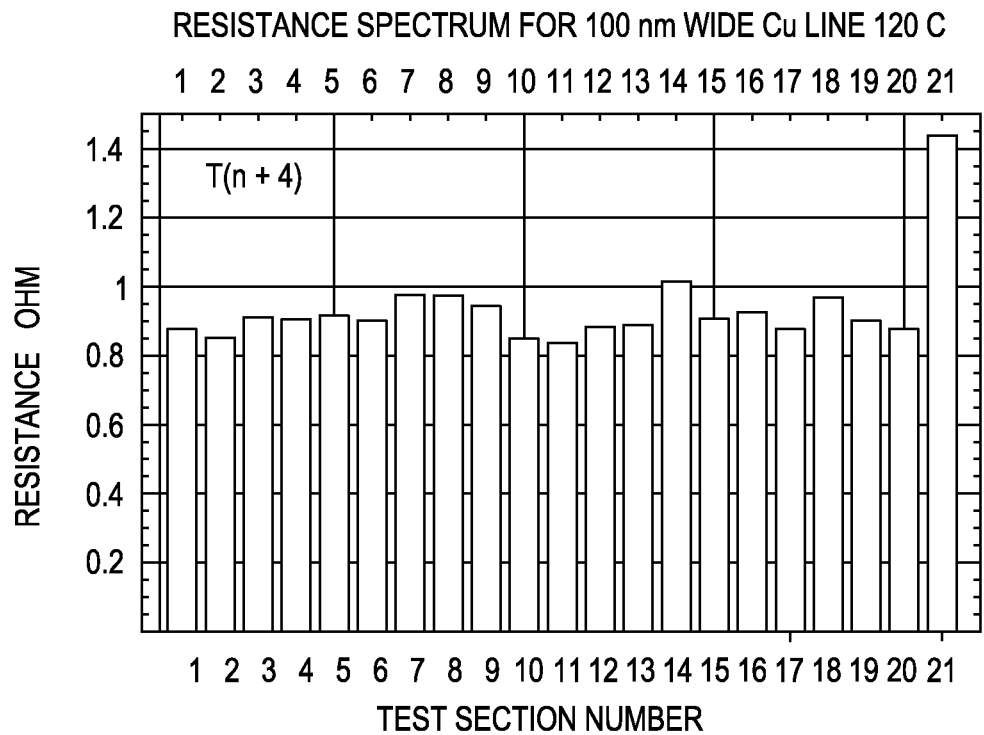
FIG. 7 is an example resistance spectrum of the electromigration test system depicted in FIG. 1A, in accordance with an embodiment of the present disclosure.

FIG. 7, depicts an example of a resistance spectrum at T(n+4). In FIG. 7, the resistance of test section 19 has decreased, but the resistance of test section 21 has increased beyond any of the previously determined resistances. FIG. 7 indicates that the void migrated from test section 19 to test section 21 between T(n+3) and T(n+4). In addition, FIG. 7 indicates that the void has continued to grow in test section 21 and/or that voids have agglomerated in test section 21. Test section 21 depicts conductive member 102 before void growth and/or agglomeration transects conductive member 102, thus breaking conductive member 102 and causing an electromigration failure in conductive member 102.

Although omitted from FIGS. 2 to 7 for simplicity, the resistance spectra can also indicate regions of extrusion. While void evolution reduces the local cross-sectional area of regions of conductive member 102, EM-induced extrusion increases the local cross-sectional area of regions of conductive member 102. An increase in local cross-sectional area reduces local current density, and consequently, reduces local resistance. In practice, resistance spectra could also show a trend that is opposite to the trend depicted in FIGS. 2 to 7. For example, a region of decreasing resistance and the propagation of a region of low resistance from approximately test section 13 to test section 1 could also be detected and depicted.

Figure 8A:
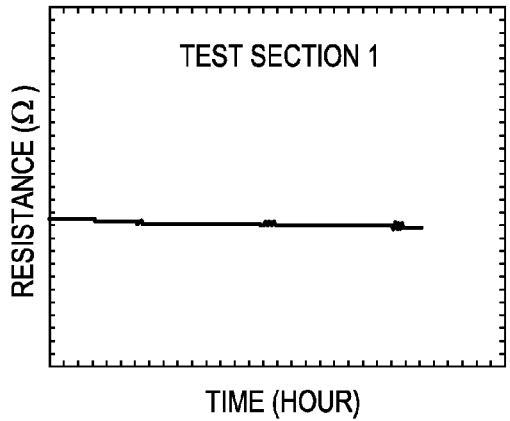
FIGS. 8A-8D depict resistance as a function of time for selected test sections of an electromigration test system, in accordance with an embodiment of the present disclosure.
Figure 8B:
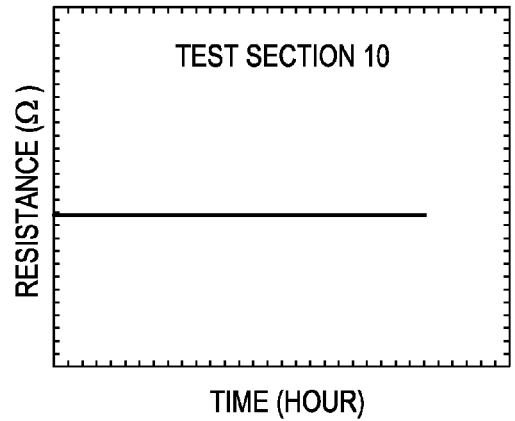
Figure 8C:
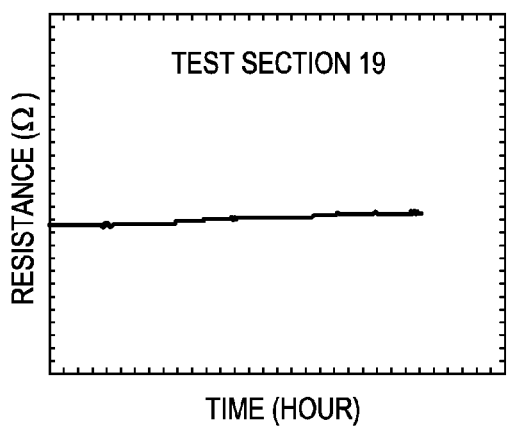
Figure 8D:
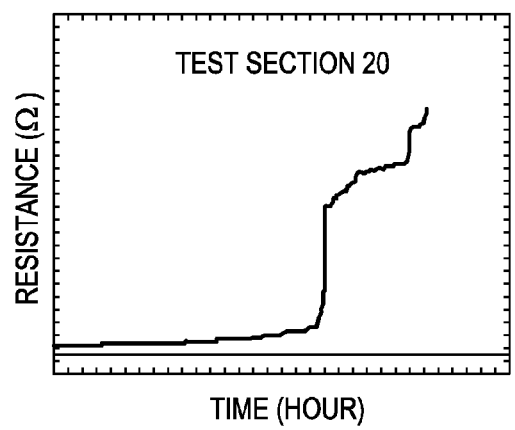

FIGS. 8A-8D depict example graphs of resistance as a function of time for selected test sections of an EM test system that has 20 test sections and is analogous to EM test system 100. For example, test section 1 extends from the cathode to a sense pin; test section 20 extends from the anode to a sense pin; and test sections 2-19 are uniformly distributed, in order, between the sense pin of test section 1 and the sense pin of test section 20. FIG. 8A depicts resistance as a function of time for test section 1 over the test period. Test section 1 shows a slight, but continuous, reduction in resistance over time. This reduction in resistance suggests that impurity segregation from copper occurred or that electromigration-induced extrusion occurred in test section one. FIG. 8B depicts resistance as a function of time for test section 10 over the test period. Test section 10 is in a middle portion of the conductive member and shows neither a substantial increase nor a substantial decrease in resistance over the test period. This result, in combination with the result from test section 1, suggests that any voids that nucleated in test section 10 during the test period were filled by migrating metal ions. FIG. 8C depicts resistance as a function of time for test section 19 over the test period. The resistance of test section 19 increases slightly over the test period. FIG. 8D depicts resistance as a function of time for test section 20 over the test period. The resistance of test section 20 increases substantially over the test period. FIGS. 8C and 8D show that voids evolved in the V2 end portion of the conductive member, although the mechanism of void evolution (e.g., void growth and/or void agglomeration) is unclear from these observations alone.

Figure 9A:
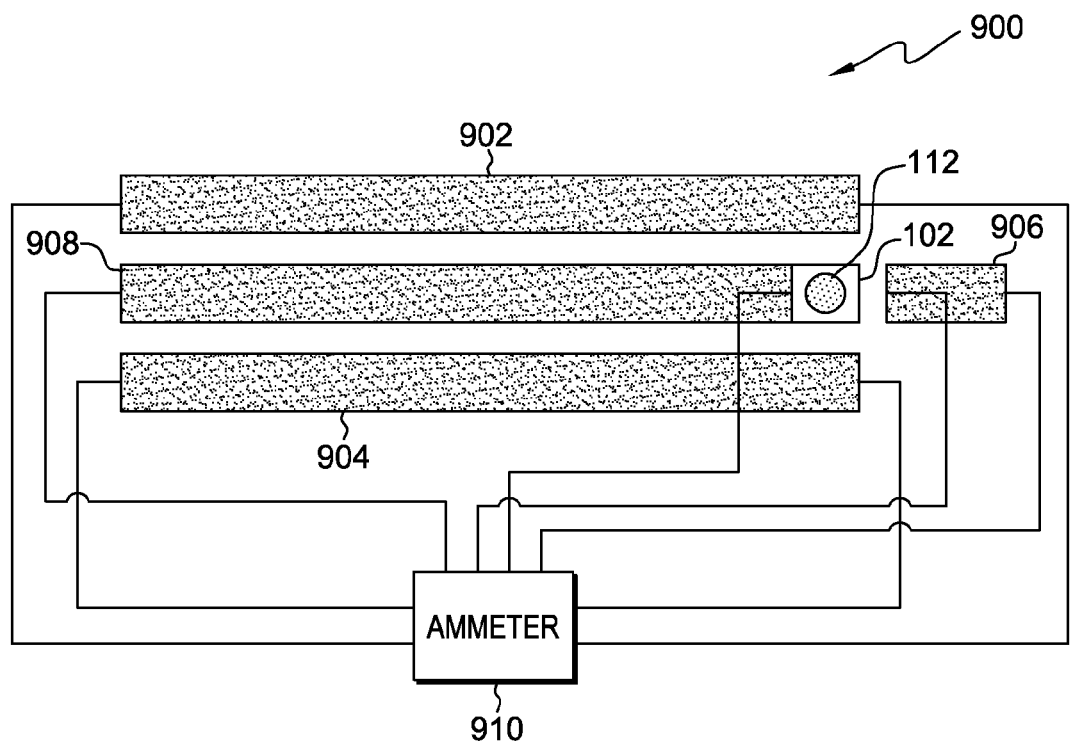
FIG. 9A is a functional block diagram that depicts electrical connections in an electromigration test system with a plurality of leakage monitors and an ammeter, in accordance with an embodiment of the present disclosure.
Figure 9B:
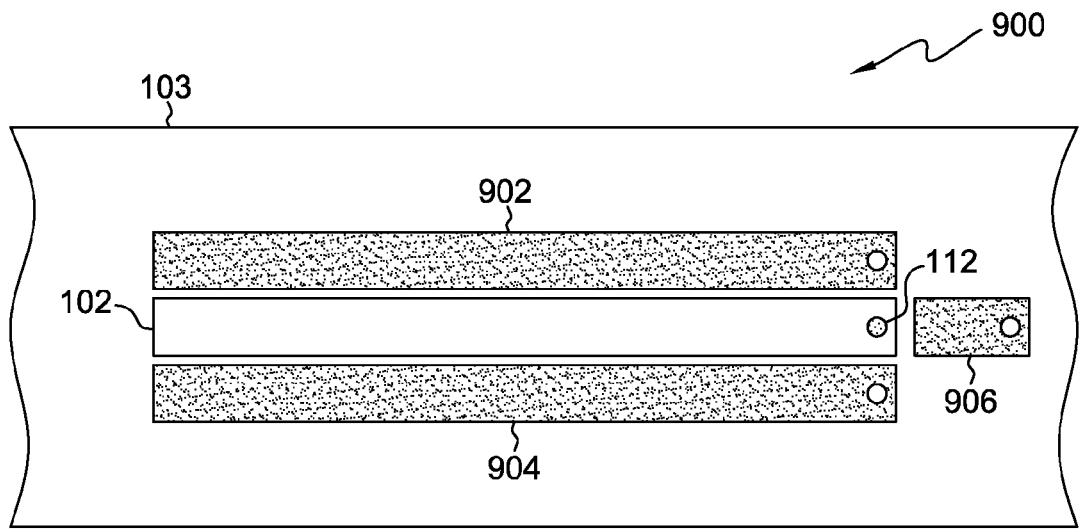
FIG. 9B is a functional block diagram that depicts a top-down view of a cross-section of a wafer that includes a substrate and a plurality of leakage monitors.
Figure 9C:
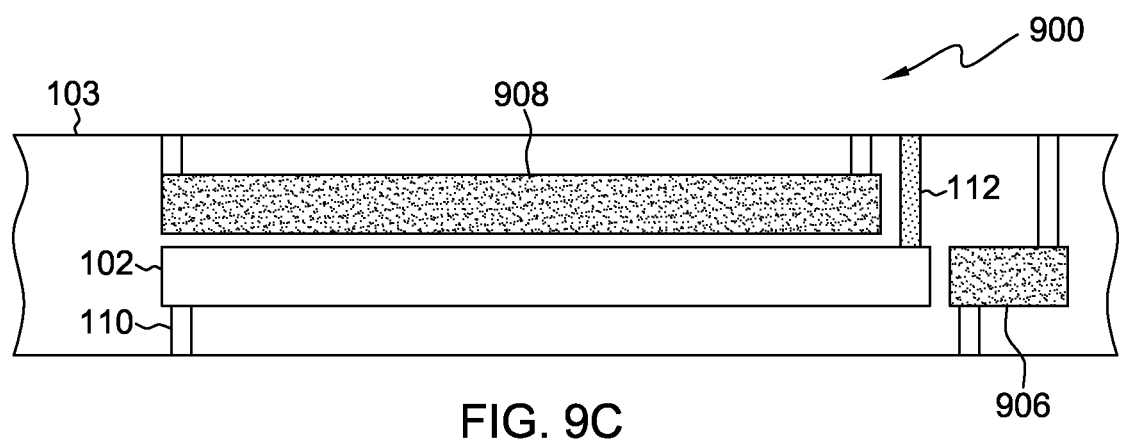
FIG. 9C is a functional block diagram that depicts an edge-on view of a cross-section of a wafer that includes a substrate and a plurality of leakage monitors.

FIGS. 9A, 9B, and 9C depict an embodiment that includes one or more devices to detect and characterize EM-induced extrusion. In this embodiment, EM-induced extrusion is detected and monitored by measuring leakage currents. Quantum tunneling enables charge carriers to tunnel through insulating regions. Tunneling charge carriers create leakage currents that are inversely proportional to the thickness of the insulating regions. EM-induced extrusion reduces the thickness of the insulating region between a test interconnect and a leakage monitor. Consequently, an increasing leakage current indicates that EM-induced extrusion is occurring.

FIG. 9A depicts electrical connections in EM test system 900, in accordance with an embodiment of the present disclosure. EM test system 900 includes leakage monitors 902, 904, 906, and 908 that are electrically connected to ammeter 910 as shown in FIG. 9A. In some embodiments, additional structures, such as vias, facilitate connections between the leakage monitors and ammeter 910. Ammeter 910 can be any device or combination of devices that can detect EM-induced leakage current(s) in the leakage monitors. In general, each of leakage monitors 902, 904, 906, and 908 is one or more conductive members. In the embodiment depicted in FIGS. 9A, 9B, and 9C, each of leakage monitors 902, 904, 906, and 908 is a single conductive member. In other embodiments, each of leakage monitors 902, 904, 906, and 908 can be a single conductive member or include one or more sub-elements, wherein each sub-element is a conductive member that is electrically connected to ammeter 910. For example, each leakage monitor of leakage monitors 902, 904 and 908 can have a number of sub-elements that are longitudinally distributed in a row between a cathode and an anode. The leakage monitors of EM test system 900 can be operatively connected to ammeter 910 to allow ammeter 910 to obtain leakage current data for each conductive member over a period of time. Accordingly, EM test system 900 can allow for a determination of an approximate position of extruded material using a method that is analogous to the method of detecting and characterizing void evolution as described herein with respect to EM test system 100.

In some embodiments, EM test system 900 is a standalone test system for testing EM-induced extrusion in interconnect analogues. In other embodiments, EM test system 900 is used in combination with EM test system 100 to characterize void evolution and EM-induced extrusion in conductive member 102. Accordingly, the elements of EM test system 900 can be operatively integrated with the elements of EM test system 100. The embodiment depicted in FIGS. 9A, 9B, and 9C, for example, includes elements of EM test system 100.

FIG. 9B is a top-down view of a cross-section of a wafer that includes substrate 103 and elements of EM test systems 100 and 900. FIG. 9B depicts leakage monitors 902, 904, and 906 embedded in substrate 103. Persons skilled in the art will understand that the relative sizes and spacing of elements in FIGS. 9A, 9B, and 9C is for illustrative purposes only. Leakage monitor 902 and leakage monitor 904 are each a conductive member that is substantially parallel to conductive member 102. Conductive member 102, leakage monitor 902, and leakage monitor 904 are substantially coplanar in a horizontal plane. Leakage monitor 902 and leakage monitor 904 are each operatively displaced horizontally from conductive member 102 in order to detect EM-induced extrusion. The embodiment depicted in FIG. 9B also includes leakage monitor 906. Leakage monitor 906 is substantially coplanar with conductive member 102, leakage monitor 902, and leakage monitor 904. Leakage monitor 906 is also substantially collinear with conductive member 102, but operatively displaced from the V2 end of conductive member 102.

FIG. 9C is a functional block diagram that depicts an edge-on view of a cross-section of a wafer that includes substrate 103 and elements of EM test systems 100 and 900. The embodiment depicted in FIG. 9C (and also FIGS. 9A and 9B) includes sensory pins 114 as depicted, for example, in FIGS. 1A and 1B. Sensory pins 114 are not shown in FIG. 9C for simplicity. Similarly, embodiments of EM test system 900 include cathode 106, anode 108, sensory taps 116, switch 118, voltmeter 120, and computer 122 as depicted, for example, in FIGS. 1A and 1B. As depicted in FIG. 9C, leakage monitor 908 is substantially parallel to conductive member 102 and substantially coplanar with conductive member 102 and leakage monitor 906 in a vertical plane. Leakage monitor 908 is operatively displaced from conductive member 102 in the vertical plane to detect leakage currents. Leakage monitor 908 is also sized and/or positioned to allow active via 112 and anode 108 to operatively connect to conductive member 102. FIG. 9C also depicts leakage element 906 in relation to conductive member 102 as described herein with respect to FIG. 9B.

In addition to hardware to detect leakage currents, EM test system 900 can include hardware and/or software to enable any one, or a combination, of leakage monitors 902, 904, 906, and 908 to function as a resistive heater or thermometer. Accordingly, leakage monitors 902, 904, 906, and 908 can be modified to perform these functions. For example, one or more leakage monitors can be connected to a thermometer and modified to function as a thermocouple. One or more thermocouples can be used to study thermal distribution along conductive member 102 during EM stress. In another example, the temperature of one or more leakage monitors is measured directly in order to estimate the temperature of the environment around conductive member 102. Persons of ordinary skill in the art will understand that increasing electrical resistance due to void evolution can result in increased heat dissipation into the environment surrounding an interconnect. Consequently, increasing ambient temperatures in the environment around conductive member 102 is another indication of void evolution. In other embodiments, one or more leakage monitors function as resistive heaters when a current is applied. One or more resistive heaters can be used to simulate the operational environment of an interconnect of an integrated circuit having a known thermal design power. Such embodiments enable the study void evolution and EM-induced extrusion under operational conditions.

What is claimed is:

1. A system for electromigration testing, the system comprising:
   a conductive member;
   a cap layer of insulative material over at least a portion of a top surface of the conductive member;
   a cathode conductively connected to a first end of the conductive member;
   an anode conductively connected to a second end of the conductive member, wherein the conductive member conductively connects the anode and the cathode;
   a current source conductively connected to the cathode and anode, wherein the current source provides a current that flows through the conductive member;
   a plurality of sensory pins disposed along a length of the conductive member between the first end and the second end of the conductive member, the sensory pins conductively connected to a bottom surface of the conductive member;
   at least one measurement device conductively connected to at least one sensory pin of the plurality of sensory pins, wherein the at least one measurement device determines a resistance of at least one portion of the conductive member; and
   a switch conductively connected to the at least one measurement device and each sensory pin of the plurality of sensory pins, wherein the switch selectively allows an electrical connection between a measurement device of the at least one measurement device, a first structure, and a second structure, and wherein the measurement device determines a resistance of a portion of the conductive member that is between the first structure and the second structure.

2. The system of claim 1, wherein the first structure is a first sensory pin of the plurality of sensory pins, and wherein the second structure is a second sensory pin of the plurality of sensory pins.

3. The system of claim 1, wherein the first structure is a first sensory pin of the plurality of sensory pins, and wherein the second structure is the cathode.

4. The system of claim 1, wherein the first structure is a first sensory pin of the plurality of sensory pins, and wherein the second structure is the anode.

5. The system of claim 1, wherein the at least one measurement device measures a voltage between the first structure and the second structure, and wherein the at least one measurement device determines the resistance based, at least in part, on a magnitude of the voltage.

6. The system of claim 1, further comprising: at least one leakage monitor, each at least one leakage monitor positioned to detect a leakage current, wherein the leakage current is an electrical current that is induced in the leakage monitor by the current that flows through the conductive member.

7. The system of claim 6, wherein the at least one leakage monitor includes a leakage monitor to which current is selectively applied in order to heat the conductive member.

8. The system of claim 6, further comprising: a thermometer, wherein the at least one leakage monitor includes a leakage monitor that is conductively connected to the thermometer such that the thermometer determines an ambient temperature at one or more points in an environment that includes the conductive member.

9. The system of claim 6, wherein the at least one leakage monitor includes a leakage monitor having a side surface that is adjacent to, and substantially parallel with, at least a portion of a side surface of the conductive member.

10. The system of claim 6, wherein the at least one leakage monitor includes a leakage monitor oriented in a substantially parallel direction to the conductive member and positioned above the cap layer.

11. The system of claim 6, wherein the at least one leakage monitor includes a leakage monitor having a length that is substantially collinear with a length of the conductive member.

12. A method for electromigration testing, the method comprising:
   causing a current to flow through a conductive member; and
   determining a resistance of at least one portion of the conductive member using at least one measurement device, and wherein:
      a cap layer of insulative material is disposed over at least a portion of a top surface of the conductive member,
      a plurality of sensory pins is disposed along a length of the conductive member between a first end of the conductive member and a second end of the conductive member,
      each sensory pin of the plurality of sensory pins is conductively connected to a bottom surface of the conductive member,
      each at least one portion of the conductive member includes at least one sensory pin of the plurality of the sensory pins, the at least one measurement device is conductively connected to at least one sensory pin of the plurality of sensory pins, and a switch is conductively connected to the at least one measurement device and each sensory pin of the plurality of sensory pins, wherein the switch selectively allows an electrical connection between a measurement device of the at least one measurement device, a first structure, and a second structure, and wherein the measurement device determines a resistance of a portion of the conductive member that is between the first structure and the second structure.

13. The method of claim 12, wherein the first structure is a first sensory pin of the plurality of sensory pins, and wherein the second structure is a second sensory pin of the plurality of sensory pins.

14. The method of claim 12, further comprising: measuring a voltage, wherein the voltage is measured between the first structure and the second structure, and wherein the at least one measurement device determines the resistance based, at least in part, on a magnitude of the voltage.

15. The method of claim 12, further comprising: determining a magnitude of a leakage current, wherein the leakage current is an electrical current that is induced in at least one leakage monitor by the current that is caused to flow through the conductive member.

16. The method of claim 15, further comprising: determining an ambient temperature at one or more points in an environment that includes the conductive member, wherein the at least one leakage monitor includes a leakage monitor that is conductively connected to a thermometer that determines the ambient temperature.

17. The method of claim 15, further comprising: heating the conductive member, wherein the at least one leakage monitor includes a leakage monitor that provides resistive heating when a current is applied.

18. An apparatus for electromigration testing, the apparatus comprising:

a plurality of conductive members embedded in a substrate, wherein each conductive member of the plurality of conductive member comprises:

a first end conductively connected to a first active via;

a second end conductively connected to a second active via; and a plurality of sensory pins disposed along a length of the conductive member between the first end and the second end of the conductive member, wherein each sensory pin has a first end that is conductively connected to a bottom surface of the conductive member, and wherein each sensory pin has a second end that is at least partially exposed;

at least one measurement device conductively connected to at least one sensory pin of the plurality of sensory pins, wherein the at least one measurement device determines a resistance of at least one portion of the conductive member; and a switch conductively connected to the at least one measurement device and each sensory pin of the plurality of sensory pins, wherein the switch selectively allows an electrical connection between a measurement device of the at least one measurement device, a first structure, and a second structure, and wherein the measurement device determines a resistance of a portion of the conductive member that is between the first structure and the second structure.

* * * * *